United States Patent [19]

Potoski et al.

[11] Patent Number: 4,461,901
[45] Date of Patent: Jul. 24, 1984

[54] PYRIDYL CONTAINING 1,2-BENZISOTHIAZOLE-3-AMINE DERIVATIVES

[75] Inventors: John R. Potoski, Pottstown; Guy A. Schiehser, Malvern; Donald P. Strike, St. Davids, all of Pa.

[73] Assignee: American Home Products Corporation, New York, N.Y.

[21] Appl. No.: 472,404

[22] Filed: Mar. 4, 1983

[51] Int. Cl.$^3$ .......................................... C07D 417/12
[52] U.S. Cl. ..................................... 546/270; 424/263
[58] Field of Search ......................................... 546/270

[56] References Cited
FOREIGN PATENT DOCUMENTS
150004  4/1980  Japan ................................. 546/270

Primary Examiner—Jane T. Fan
Attorney, Agent, or Firm—George Tarnowski

[57] ABSTRACT

Compounds of the formula:

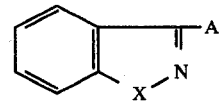

wherein
X is $SO_2$, SO or S; and
A is an amine selected from the group:

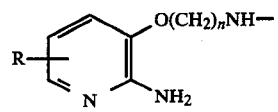

or

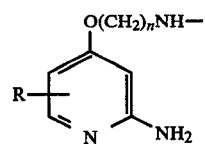

wherein R is hydrogen, (lower)alkyl, (lower)alkoxy or halo;
n is 2–4; and
the pharmacologically acceptable salts thereof are disclosed.

3 Claims, No Drawings

PYRIDYL CONTAINING 1,2-BENZISOTHIAZOLE-3-AMINE DERIVATIVES

This invention relates to new benzo-fused heterocyclic compounds having a selective action on $H_2$ histamine receptors and which exhibit gastric acid secretion.

It has been postulated that the physiologically active compound histamine, which occurs naturally within the animal body, is able to combine, in the course of exerting its activity, with certain specific receptors of which there are at least two distinct and separate types. The first has been named the $H_1$ receptor (Ash and Schild, Brit. J. Pharmac., 1966, 27, 427) and the action of histamine at this receptor is blocked (antagonized) by classical "antihistamine" drugs such as mepyramine (pyrilamine). The second histamine receptor has been named the $H_2$ receptor (Black et al., Nature, 1972, 236, 385) and the action of histamine at this receptor is blocked by drugs such as cimetidine. It is known that one of the results of the blockage of the action of histamine at the $H_2$ receptor is the inhibition of the secretion of gastric acid and a compound which possesses this ability is therefore useful in the treatment of peptic ulcers and other conditions caused or exacerbated by gastric acidity, including stress ulcers and gastrointestinal bleeding due to trauma.

The commercialization of cimetidine and subsequent follow-up pharmacological research in patients has demonstrated that cimetidine is a drug with limitations, such as short duration of action, anti-androgenic activity, and a tendency to cause confusional states in elderly patients. Obviously, much intensive research has been carried out to find improved $H_2$ antagonists. Indeed, selective $H_2$ antagonists having greater activity than cimetidine have been discovered. Among the better known new $H_2$ antagonists are ranitidine (disclosed in U.S. Pat. No. 4,128,658) having the structure:

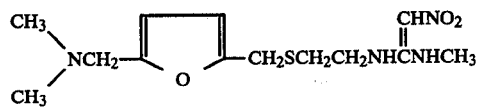

tiotidine (U.S. Pat. No. 4,165,378) having the structure:

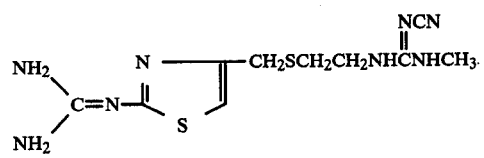

and compounds such as those disclosed in U.S. Pat. No. 3,920,822 having the structure:

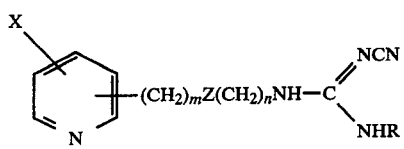

as well as closely related compounds disclosed in U.S. Pat. Nos. 4,154,838 and 4,282,224.

There has now been discovered a novel group of compounds, with potent $H_2$ receptor antagonist activity, having the following formula:

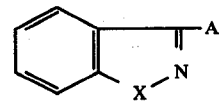

wherein X is $SO_2$, SO or S, and A is an amine selected from the group:

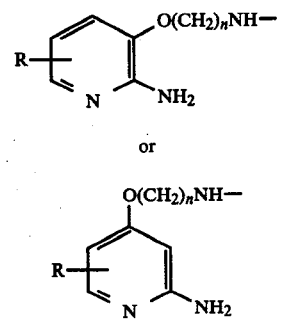

wherein
R is hydrogen, (lower)alkyl, (lower)alkoxy or halo;
n is 2–4; and
the pharmaceutically acceptable salts thereof.

The term "halo" refers to fluoro, chloro and bromo. The terms "lower alkyl" and "lower alkoxy" refer to moieties having 1 to 6 carbon atoms in the carbon chain.

The compounds of the invention can be readily prepared by reacting the chloride of a benzisothiazole with the desired amine according to the following reaction sequence.

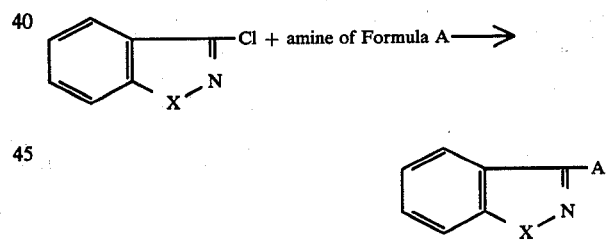

where X and A are as defined hereinbefore. The benzisothiazoles are known compounds which are readily available or which can be prepared by known methods. Thus, for example, the compound

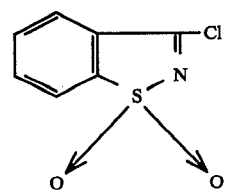

is pseudo saccharin chloride, and can be prepared according to the method of Stephen et al., J. Chem. Soc., 1957, 490–92. The amines of formula A can be readily prepared by known methods, such as for example, according to the following reaction sequence:

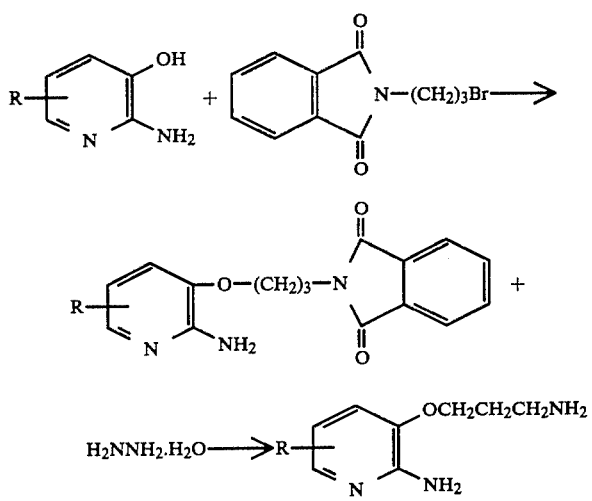

wherein R is as defined hereinbefore.

The compounds of the invention readily form pharmacologically acceptable salts with both inorganic and organic acids, such as hydrochloric, hydrobromic, sulfuric, nitric, phosphoric, acetic, maleic, fumaric, citric and the like.

The compounds of the invention have potent histamine $H_2$-blocking activity and can be used in the treatment of conditions where there is hypersecretion of gastric acid, such as in gastric and peptic ulceration, and other conditions caused or exacerbated by gastric acidity such as stress ulceration or gastric intestinal bleeding due to trauma.

The compounds of the invention can be administered orally or parenterally or by suppository, of which the preferred route is the oral route. They may be used in the form of the base or as a pharmacologically acceptable salt. They will in general be associated with a pharmaceutically acceptable carrier or diluent, to provide a pharmaceutical composition.

The compounds of the invention can be administered in combination with other active ingredients, e.g. conventional antihistamines if required. For oral administration the pharmaceutical composition can most conveniently be in the form of capsules or tablets, which may be slow release tablets. The composition may also take the form of a dragee or may be in syrup form.

A convenient daily dose by the oral route would be of the order of 100 mg to 1.2 per day, in the form of dosage units containing from 20 to 200 mg per dosage unit. A convenient regimen in the case of a slow release tablet would be twice or three times a day.

Parenteral administration may be by injections at intervals or as a continuous infusion. Injection solutions may contain from 10 to 100 mg/ml of active ingredient.

The histamine $H_2$-antagonist activity of the compounds of the invention may be demonstrated by the ability of the compounds to inhibit the histamine-induced positive chronotropic response in the spontaneously beating right atrium of the guinea pig heart, as well as by activity in other more generalized procedures, such as the modified Shay procedure of pylorus ligation for the study of rat gastric secretion. The procedures for these tests and the results for some of the compounds of the invention are presented at the end of the following examples, which will serve to illustrate the present invention.

EXAMPLE 1

Preparation of 3-chlorobenzisothiazole-1,1-dioxide (ψ-saccharin chloride)

Following the procedure of Stephen et al., *J. Chem. Soc.*, 1957, 490–92, 1 mol of saccharin (1,2-benzisothiazol-3(2H)-one 1,1-dioxide) is heated with 1.1 mol phosphorus pentachloride at 170° C. for 1.5 hours. Phosphorus oxychloride is removed at 60°/30 mm and the yellow crystalline residue of ψ-saccharin chloride and o-cyanobenzene sulfonyl chloride is treated with ether in which the latter is soluble. The sparingly soluble ψ-saccharin chloride in a yield of 28% is collected and crystallized from ether as white needles, m.p. 132°–137° C.

EXAMPLE 2

N-[3-[(2-amino-3-pyridinyl)oxy]propyl]-1,2-benzisothiazol-3-amine 1,1-dioxide, hydrochloride, hemihydrate A. To a stirred suspension of 4.0 g. (0.10 mole, 60% in nujol) of sodium hydride in 240 ml of dimethylformamide is added 11.0 g (0.10 mole) of 2-amino-2-hydroxypyridine. The mixture is stirred mechanically for 2 hours at room temperature under a nitrogen atmosphere. To the stirred mixture is then added 26.8 g (0.10 mole) of N(3-bromopropyl)phthalimide. After 3 hours, the reaction solution is poured into ice water and the aqueous mixture is filtered and dried to give 22 g of crude product. Recrystallization from ethyl acetate-hexane gives 19.14 g of product with m.p. 136°–140° C. TLC of the product shows 1 spot.

B. 2-Amino-3-(3-aminopropoxy)pyridine

A mixture of 14.85 (0.050 mole) of the product of A above and 200 ml of ethanol is heated and stirred until all of the solid dissolves. The heating is stopped but stirring is continued while 5.0 ml (0.10 mole) of hydrazine hydrate is added. After 15 minutes a white solid forms and the reaction mixture is allowed to stand overnight at room temperature. Filtration of the mixture gives a white solid which is dissolved in water and basified with concentrated aqueous sodium hydroxide. The aqueous solution is extracted several times with ethyl acetate. The extracts are dried (MgSO$_4$), concentrated and distilled to give 3.1 g of product with b.p. 150°–170° C. at 3 MM.

TLC (silica eluted with MeOH containing 1% NH$_4$OH) shows 1 spot.

C. To a refluxing solution of 1.67 g (0.010 mole) of the product of B above and 2.0 ml of triethylamine in 50 ml of chloroform is added a solution of 2.01 g (0.010 M) pseudo saccharyl chloride in 20 ml of chloroform. After the addition is completed, the reaction mixture is cooled and filtered to give 2.7 g of white solid with m.p. 227°–232° C. The solid is suspended in ethanol and acidified by addition of ethanolic hydrogen chloride. The solid dissolves on the hydrogen chloride addition and after a few minutes a white precipitate forms. Filtration gives 2.75 g of the hydrogen chloride salt of the product with m.p. 270°–274° C. Recrystallization from ethanol-water gives 2.25 g with m.p. 277°–278° C.

Analysis for: $C_{15}H_{16}N_4O_3S \cdot HCl \cdot \frac{1}{2}H_2O$: Calculated: C, 47.68; H, 4.80; N, 14.82; Found: C, 47.61; H, 5.01; N, 14.70

EXAMPLE 3

N-[3-[(2-amino-4-pyridinyl)oxy]propyl]-1,2-benzisothiazol-3-amine 1,1 dioxide, hydrochloride, hemiethanolate A. A mixture of 1.2 g (0.0526 GA) of sodium in 9.35 g of 3-aminopropanol is heated at 100° C. in an oil bath, with stirring under a nitrogen atmosphere for 18 hours. The mixture is cooled to 50° C. and 6.2 g (0.048 mole) of 2-amino-4-chloropyridine is added. The mixture is then heated gradually on an oil bath to 140° C. at which point an exotherm occurred, causing the oil bath temperature to rise to 165° C. within a few minutes. During this time, all of the 2-amino-4-chloropyridine dissolves and a white precipitate forms. The reaction mixture is cooled. The mixture is triturated with hot ethyl acetate and filtered. The combined filtrates are concentrated to give 7.0 g of white solid. Recrystallization from ethanol gives 4.0 g of product with m.p. 98°–101° C.

B. By using the same procedure as described in Example 2C above, from 1.67 g (0.010 mole) of the product described in A above there is obtained 2.70 g of product as a free base with m.p. 230°–240° C. Conversion of this to its hydrogen chloride salt by the procedure described in Example 2C, gives 1.90 g of product hydrochloride with m.p. 248°–249° C. on recrystallization from ethanol-water.

Analysis for: $C_{15}H_{16}N_4O_3S \cdot HCl \cdot \frac{1}{2}C_2H_5OH$: Calculated: C, 49.04; H, 5.14; N, 14.30; Found: C, 48.75; H, 5.20; N, 14.69

EXAMPLE 4

The guinea pig heart atrium test is carried out as follows.

A guinea pig right atrium is suspended at 1 g tension (isometric) in the thermostatically controlled (32° C.) tissue bath (10 ml) containing oxygenated (95% $O_2$; 5% $CO_2$) Krebs-Haenseleit buffer (pH 7.4). The tissue is allowed to stabilize over 1 hour. Individual contractions are recorded with a force-displacement transducer through a strain gauge coupler. A control dose-response curve to histamine in the above described tissue bath is obtained after which the tissue is washed 3 times and allowed to re-equilibrate to basal rate. The test compound is added to the tissue bath at the desired final concentration. Thirty minutes after addition of the compound, a fresh histamine dose response curve is again obtained. Then the response to histamine in the presence of antagonist is compared to the histamine control response. This procedure is repeated, using fresh tissues, for each concentration of antagonist tested. The result is expressed as the apparent dissociation constant (pA$_2$) of the H$_2$ antagonist as determined by standard procedures. Cimetidine is used as the standard for this test.

The results for two of the compounds of the invention are as follows:

| Compound or Example No. | pA$_2$ Value |
| --- | --- |
| Cimetidine | 6.5 |
| 2 | 8.0 |
| 3 | 8.0 |

The results show that the compounds of the invention are extremely active H$_2$ antagonists, being significantly more active than the standard compound cimetidine.

EXAMPLE 5

The procedure for testing gastric secretion in the rat, a modification of the procedure of Shay et al., *Gastroenterology*, 26, 906–13 (1954) is carried out as follows.

Male Charles River rats weighing 200–300 grams are deprived of food but not water for 24 hours prior to use. Water is, however, withheld during the experiment. The rats are weighed, anesthetized, and the pylorus ligated according to the method of Shay et al. Treatment or vehicle control is then administered interduodenally (i.d.). Rats are housed 2/cage and sacrificed with $CO_2$ four hours after ligation. The stomachs are removed, rinsed, and contents emptied into a graduated centrifuge tube. The tubes are centrifuged for 20 minutes at 2,000 RPM and the volume of gastric juice recorded. Any samples obviously contaminated by feces, food or hemolysis are eliminated. An aliquot of each is frozen for later analysis of $Na^+$, $K^+$ and $Cl^-$ concentration. The pH is measured and 1 ml of gastric juice is titrated with 0.1N NaOH to a pH of 7.0–7.4. Titratable acid output is calculated in microequivalents and the percent inhibition of acid output is calculated as follows:

$$\% \text{ Inhibition of Acid Output} = \frac{\text{Acid Output (control)} - \text{Acid Output (drug)}}{\text{Acid Output (control)}} \times 100$$

The test results for a compound of the invention is as follows:

| Compound of Example No. | Dose (mg/kg) | % Inhibition |
| --- | --- | --- |
| 3 | 32 | 57 |

The results show that compounds of the invention have significant activity in inhibiting gastric acid secretion.

What is claimed is:

1. A compound having the formula:

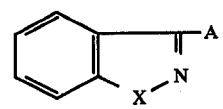

wherein
X is $SO_2$, SO or S; and
A is an amine selected from the group:

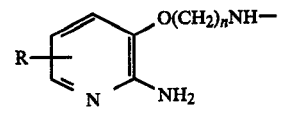

or

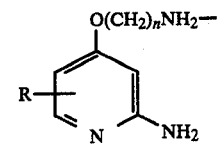

wherein R is hydrogen, (lower)alkyl, (lower)alkoxy or halo;

n is 2–4; or a pharmaceutically acceptable salt thereof.

2. The compound of claim 1, having the name N-[3-[(2-amino-3-pyridinyl)oxy]propyl]-1,2-benzisothiazol-3-amine 1,1-dioxide.

3. The compound of claim 1, having the name N-[3-[(2-amino-4-pyridinyl)oxy]propyl]-1,2-benzisothiazol-3-amine 1,1-dioxide.

* * * * *